United States Patent [19]

Newman

[11] 4,283,952
[45] Aug. 18, 1981

[54] FLAW DETECTING DEVICE AND METHOD

[75] Inventor: John W. Newman, Wayne, Pa.

[73] Assignee: Laser Technology, Inc., Norristown, Pa.

[21] Appl. No.: 40,678

[22] Filed: May 21, 1979

[51] Int. Cl.³ .................................. G01H 13/00
[52] U.S. Cl. .............................. 73/579; 73/1 DV
[58] Field of Search ............. 73/1 DV, 579, 597, 598, 73/580, 581, 582, 583, 584, 662, 663

[56] References Cited

U.S. PATENT DOCUMENTS

| | | | |
|---|---|---|---|
| 2,612,772 | 10/1952 | McConnell | 73/598 |
| 3,043,132 | 7/1962 | Schubring | 73/579 |
| 4,122,723 | 10/1978 | Levizzari et al. | 73/579 |
| 4,122,724 | 10/1978 | Geithman et al. | 73/588 |

FOREIGN PATENT DOCUMENTS

| | | |
|---|---|---|
| 707398 | 3/1957 | United Kingdom |
| 1332898 | 10/1973 | United Kingdom |
| 1352606 | 5/1974 | United Kingdom |
| 1422420 | 1/1976 | United Kingdom |

OTHER PUBLICATIONS

Krautkraner "Ultrasonic Testing of Materials," 2nd Edition, 1977, Springer-Verlag, pp. 265, 266.

Primary Examiner—Stephen A. Kreitman
Attorney, Agent, or Firm—Harding, Earley & Follmer

[57] ABSTRACT

The method and apparatus of the invention simultaneously induces the same variable frequency mechanical vibrations in a test part and a standard. The vibrations of the two are converted to signals which are either displayed for comparison purposes or automatically analyzed for differences. Advantageously, the signals are electrical signals providing spectra which are analyzed for differences in amplitudes produced by the signals. Where the parts are separately supported, they are held with substantially the same force and are maintained against the vibration inducing mechanism with the same force. Where accelerometers are used, they are held with substantially the same force against the vibrating parts.

14 Claims, 11 Drawing Figures

FLAW DETECTING DEVICE AND METHOD

TECHNICAL FIELD

This invention is in the field of non-destructive testing.

BACKGROUND OF THE PRIOR ART

It is known that similar parts will produce similar patterns of vibration amplitudes over a range of frequencies with the greatest amplitudes being at the resonant frequencies. When one of these parts has one or more defects, a substantial variation in the pattern will be produced and it is known to use this variation to detect flaws in production parts.

The above-known principles were employed in U.S. Pat. No. 3,043,132 which is incorporated herein by reference. In the case of this patent, the resonant frequencies of a part are first obtained and then used to determine circuit values in order to provide for output signals indicating whether or not a part being tested has resonances corresponding to a standard. In accordance with this invention, all such preliminary computations are eliminated by simultaneously comparing the part being tested with a standard part known to be free of defects or with another portion of the part being tested expected to have the same amplitude pattern as the portion being tested.

BRIEF SUMMARY OF THE INVENTION

The method and apparatus of the invention simultaneously induces the same variable frequency mechanical vibrations in a test part and a standard. The vibrations of the two are converted to signals which are either displayed for comparison purposes or automatically analyzed for differences. Advantageously, the signals are electrical signals providing spectra which are analyzed for differences in amplitudes produced by the signals. Where the parts are separately supported, they are held with substantially the same force and are maintained against the vibration inducing mechanism with the same force. Where accelerometers are used, they are held with substantially the same force against the vibrating parts.

DETAILED DESCRIPTION

A testing device 2 (FIG. 1) in accordance with the invention has a base 4 secured to a flange member 6 by screws 7. Transversely mounted blocks 10, 12 and 14 are secured to the top of base 4 and support spaced rods 16 and 18 above base 4. A pair of carriages 22,22 are mounted on rods 16 and 18.

The following is a description of each carriage 22 and its closely associated parts. A pair of bores 30,30 each has at either end a sleeve 32 for slidably engaging, respectively, rods 16 and 18. A pair of transverse blocks 34 and 36 are secured to opposite ends of the top of carriage 22 by machine screws indicated at 38. Blocks 34 and 36 support a pair of spaced parallel rods 40,40. A chuck member 44 is mounted for longitudinal sliding on rods 40 and has a jaw member 46 (FIG. 4) adapted to cooperate with an opposed jaw member 48 mounted on transverse block 36. Chuck member 44 has a hollow interior 52 containing a large nut 54 adapted to receive the threaded portion 56 of a shaft 58. A handle 62 has a hub 63 fixedly secured to shaft 58 at one end thereof for rotating it and the other end of shaft 58 is supported for free rotation and longitudinal movement in an opening 64 in chuck member 44. A compression coil spring 66 surrounds shaft 58. Spring 66 has one end abutting a collar 68 secured to shaft 58 and the other end contained in a recess 70 in transverse block 34. Shaft 58 passes freely through an opening 72 in chuck member 44, recess 70 and an opening 74 in transverse block member 34. Nut 54 has a pair of upstanding transverse flanges 80 and 82 between which lies a cam 84. Flanges 80 and 82 are adapted to engage chuck member 44 to prevent nut 54 from rotating. Cam 84 is fixedly secured to a vertical shaft 86 carried by a hub 88 to which is secured a handle 90.

Figures 4, 5:
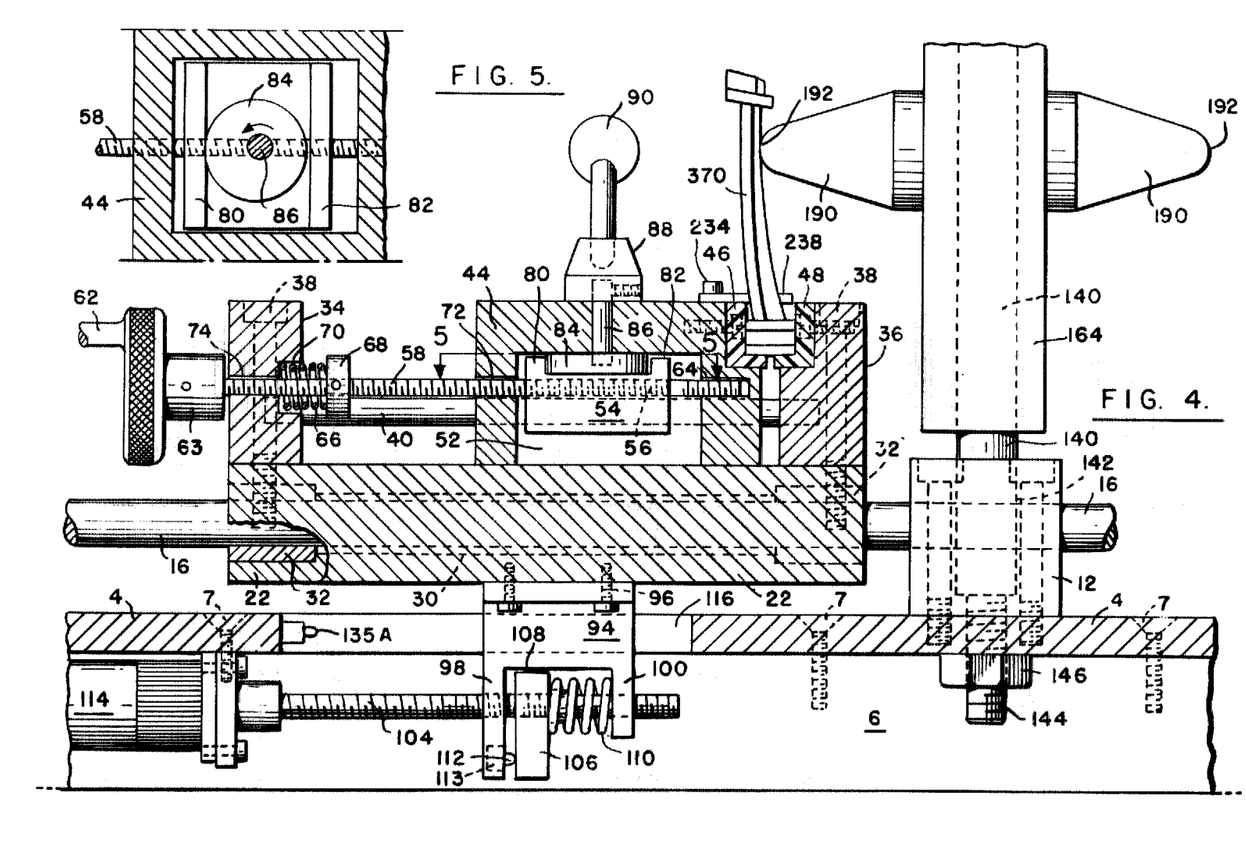
FIG. 4 is an enlarged elevational view of the device of FIG. 1, partially broken away, showing details of a carriage.
FIG. 5 is a horizontal section, partially broken away, taken on the plane indicated by the line 5—5 in FIG. 4.

Each carriage 22 has secured to its center line a depending U-shaped bracket 94 by machine screws 96 and has spaced depending arms 98 and 100. A threaded shaft 104 passes freely through arms 98 and 100 and is threaded to a nut 106, the top 108 of which is flat and engages bracket 94 to prevent rotation of nut 106. A compression coil spring 110 surrounds shaft 104 having one end in engagement with nut 106, and the other end in engagement with arm 100. Nut 106 is adapted to engage button 112 of a switch 113 recessed in arm 98. Shaft 104 is driven by a reversible motor 114. Bracket 94 passes freely through a longitudinal opening 116 in base 4 (FIG. 4).

Figure 9:
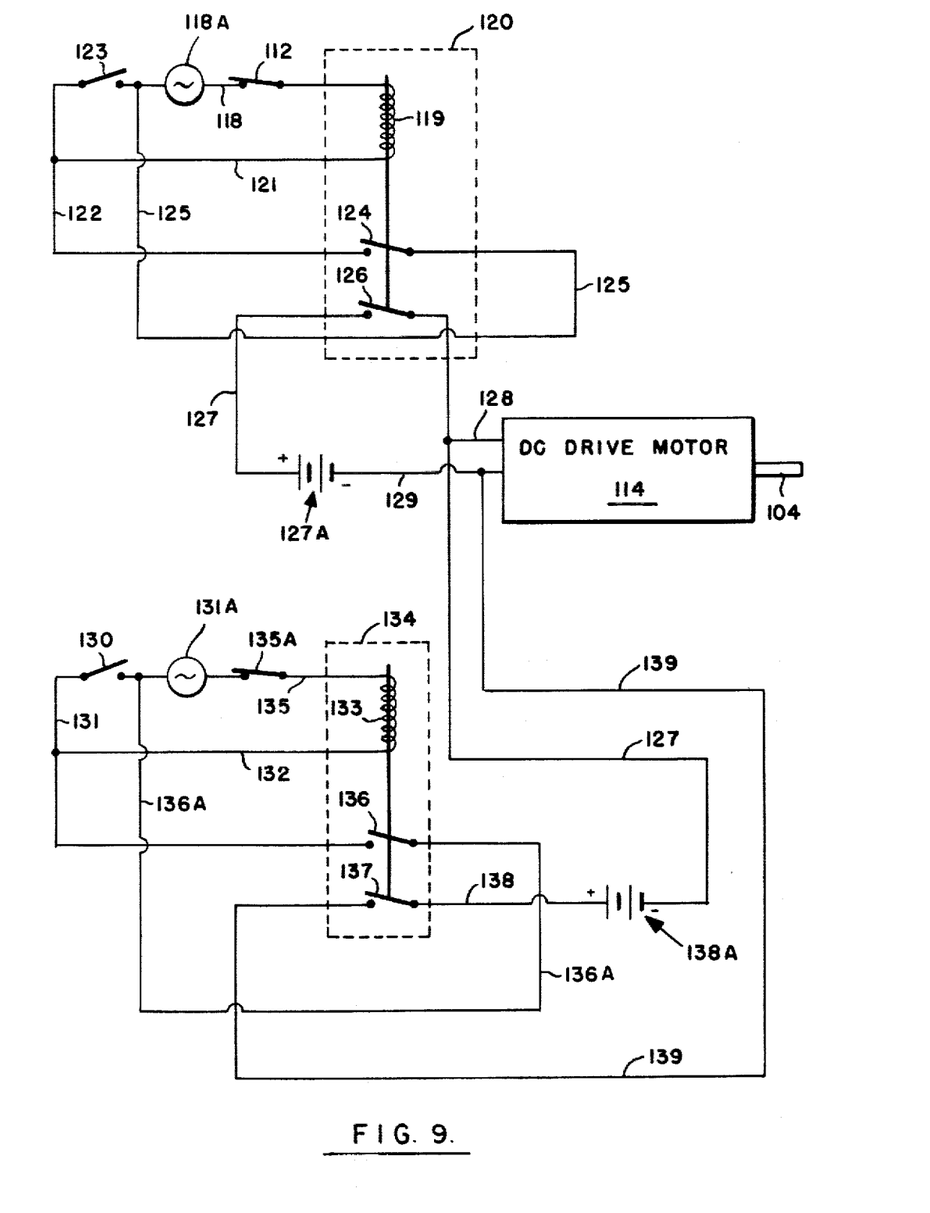
FIG. 9 is a wiring diagram of the motor circuit of the device of FIG. 1.

A control curcuit which is associated with each motor 114 is shown in FIG. 9. Normally closed switch 112 is in line 118 which is connected to coil 119 of a latching control relay 120. The other side of coil 119 is connected to line 121 which is connected to line 122 which contains a normally open momentary starting switch 123 and is connected to a source of 12 volt alternating current indicated at 118A. Normally open switch member 124 of relay 120 connects line 122 to line 125, the other end of line 125 being connected to line 122 between switch 123 and power source 118A. Normally open switch member 126 of relay 120 is in line 127 which is connected to the positive side of a 12 volt direct current source 127A and to line 128 which is connected to motor 114. The negative side of power source 127A is connected to line 129 which is also connected to motor 114. This circuitry provides for the driving of motor 114 to move the associated carriage 22 in the direction of the associated horn 190.

To provide for the driving of motor 114 in the reverse direction for the return of carriage 22 to its starting position, a momentary normally open starting switch 130 is in line 131 which is connected to one side of a 12 volt alternating current source 131A. Line 131 is connected to line 132 which in turn is connected to one end of coil 133 of a latching control relay 134. The other end of coil 133 is connected to line 135 which contains a normally closed switch 135A and is connected to the other side of the power source 131A. Normally open switch element 136 of relay 134 is connected to line 131 and to line 136A which is connected to line 131 between switch 130 and power source 131A. Switch element 137 of relay 134 is connected to line 138 which is connected to the positive side of a 12 volt direct current power source 138A and to line 139 which is connected to line 129 and hence to motor 114. The negative side of power source 138A is connected to motor 114 through line 127 and 128. Power source 138A when connected to motor 114 is in the reverse sense from power source 127A and hence will cause motor 114 to rotate in a direction the reverse of that caused by power source 127A.

It will be seen that the momentary closing of switch 123 will energize relay coil 119 which will close switch element 124 causing line 125 to be connected to line 122 which through line 121 will maintain the coil 119 energized providing a relay holding circuit. At the same time, the closing of switch element 126 will connect lines 127 and 128 causing motor 114 to drive in the direction to move carriage 22 towards its associated horn 190. Until the compression of spring 110 by nut 106 results in the movement of element 106 away from switch 112 permitting switch 112 to open and open the circuit to coil 119 thus deenergizing coil 119 and opening switches 124 and 126 to stop motor 114.

To drive carriage 22 in the opposite direction switch 130 is momentarily closed energizing coil 133 of relay 134 and closing relay switch member 136 which maintains coil 133 energized by connecting line 131 to line 136A, line 131 being connected to coil 133 by line 132. Simultaneously, switch element 137 is closed connecting line 138 to line 139 which is connected to line 129, line 127 being connected to line 128, causing motor 114 to drive in the reverse direction causing the associated carriage 22 to move away from its associated horn 190 until bracket 94 engages normally closed switch 135A to open it and deenergize coil 133 to open switch elements 136 and 137 to stop the rotation of motor 114. Switch 135A reopens when bracket 94 next moves away from switch 135A.

Figure 1:
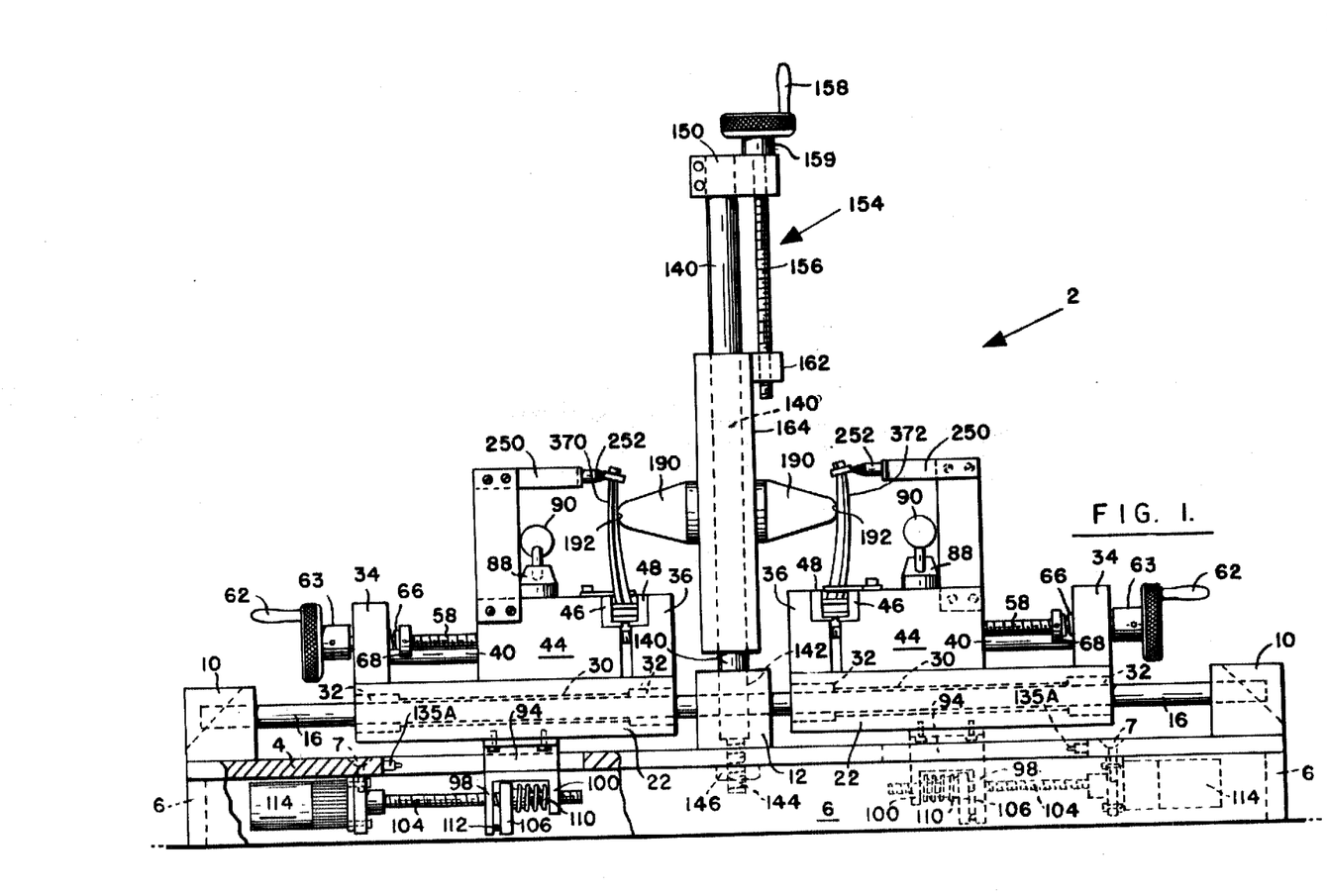
FIG. 1 is a front elevation of a flaw detecting device in accordance with the invention, partially broken away.
Figure 2:
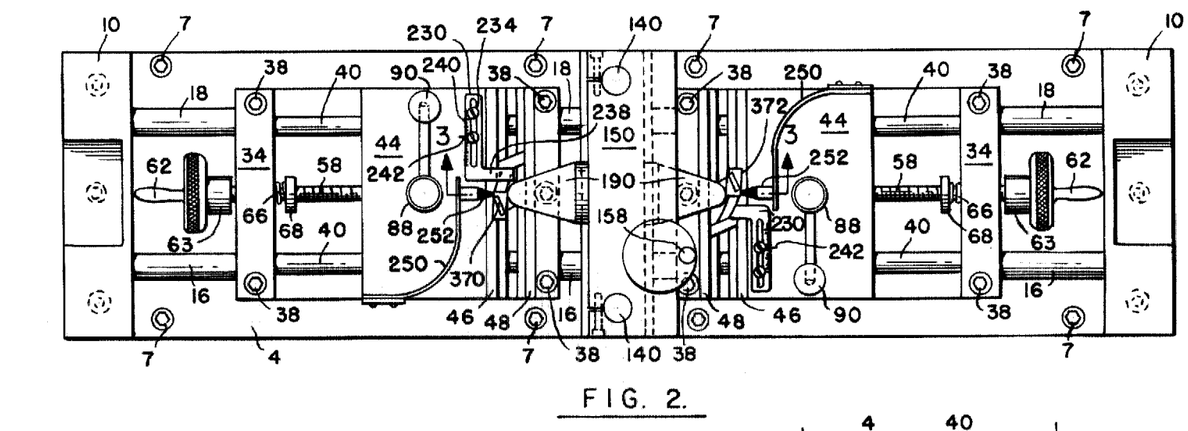
FIG. 2 is a top plan view of the device of FIG. 1.
Figures 3, 3A:
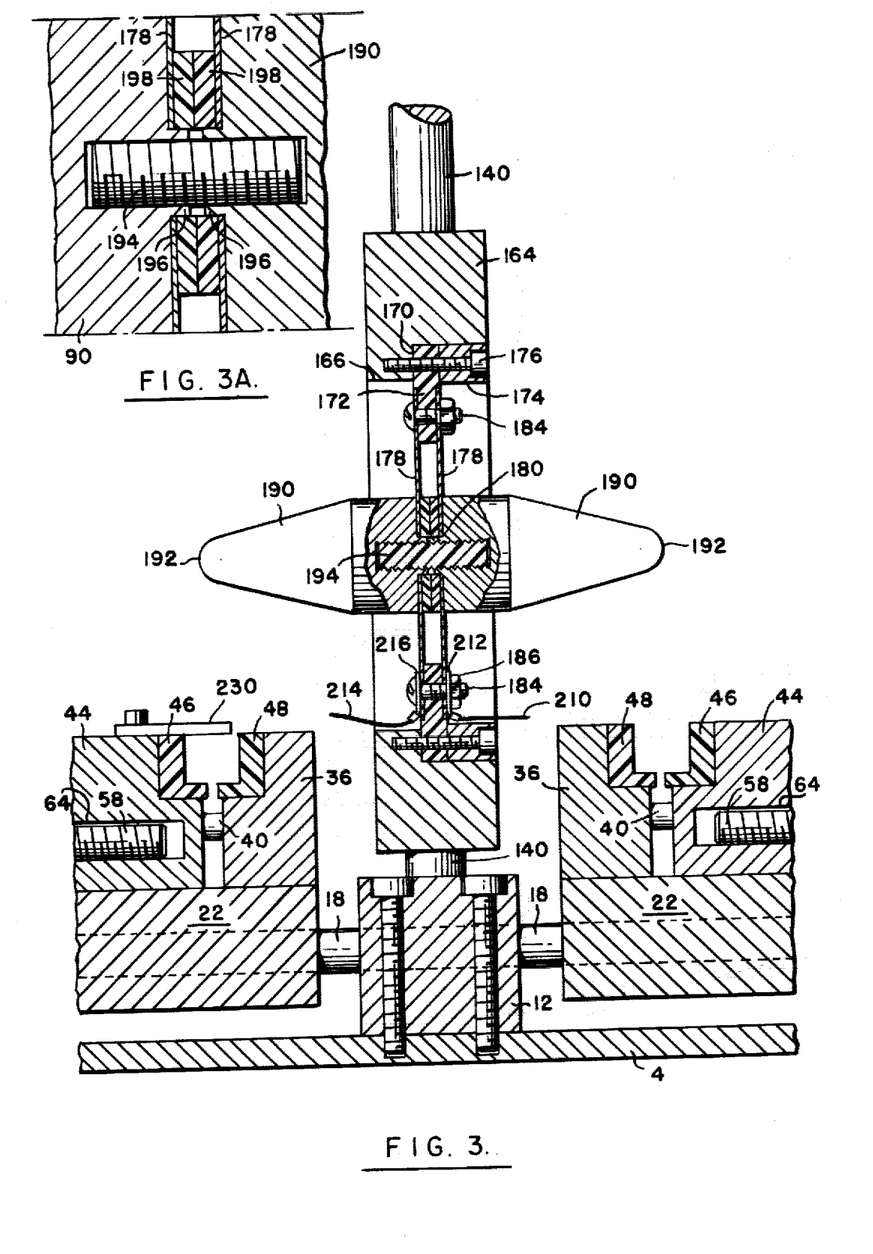
FIG. 3 is a vertical section, partially broken away, taken on the plane indicated by the line 3—3 in FIG. 2.
FIG. 3A is a vertical section, partially broken away, through the crystals and horns of the device of FIG. 1.

A pair of vertical posts 140,140 (FIG. 2) is each received in an opening 142 in transverse block member 12 and each has a reduced threaded portion 144 passing through the block 12 and base 4 (one shown in FIGS. 1 and 4). A nut 146 secures each post 140. A transverse tie member 150 is secured to the upper end of each post 140. A rod 154 has a threaded portion 156 and is rotatable by a handle 158 connected to its upper end (FIG. 1). Handle 158 has a nut 159 resting on member 150 and rod 154 passes freely through member 150. The threaded portion 156 is threaded to a bracket 162 integral with a plate 164 mounted for vertical sliding on posts 140,140. Plate 164 has a central cylindrical opening 166 (FIG. 3). Plate 164 has a stepped portion 170 adjacent opening 166 in which an insulator ring 172 is secured by a securing ring 174 and machine screws 176. A pair of conducting metal plates 178,178, for example aluminum, each having a central opening 180, are secured to insulator ring 172 by insulating bolts 184 and insulating nuts 186 of, for example, nylon.

A pair of opposed drive horns 190,190 each having a nose 192 are secured together by a threaded insulator 194 of for example nylon. Each drive horn 190 has a peripheral hollow boss 196 (FIG. 3A) and each of these bosses 196 supports a piezoelectric crystal 198 (typical are: ceramic piezoelectric crystal made of silver faced PZT by Vernitron). Crystals 198 abut each other and are held in tight contact with the adjacent plates 178 by the horns 190,190. The positive faces of the crystals both face in the same direction, namely, to the right as viewed in FIG. 3A. A wire lead 210 is connected to a connection member 212 which is held against one plate 178 by insulator bolt 184 and nut 186. A wire lead 214 is connected to a connector 216 which is held tightly against the other plate 178 by bolt 184.

Figure 2A:
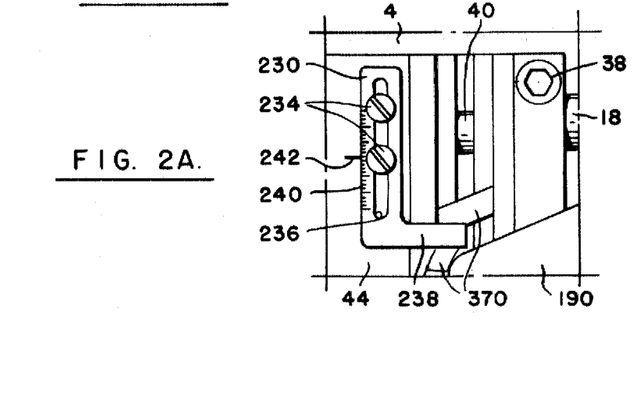
FIG. 2A is an enlarged view of a part guide of the device of FIG. 1.

Accurate positioning of the parts to be vibrated is accomplished by a pair of guides 230,230. Each guide 230 is secured to a chuck member 44 by machine screws 234 passing through a slot 236 in guide member 230 to permit the transverse adjustment of guide member 230. Guide member 230 has an arm 238 adapted to bear against a part to be tested. The accurate adjustment of each guide 230 is accomplished by the setting indicia indicated at 240 against a line 242 on chuck member 44.

Each chuck member 44 has one end of a spring steel strip 250 secured thereto with an accelerometer 252 secured to its other end.

Figure 6:
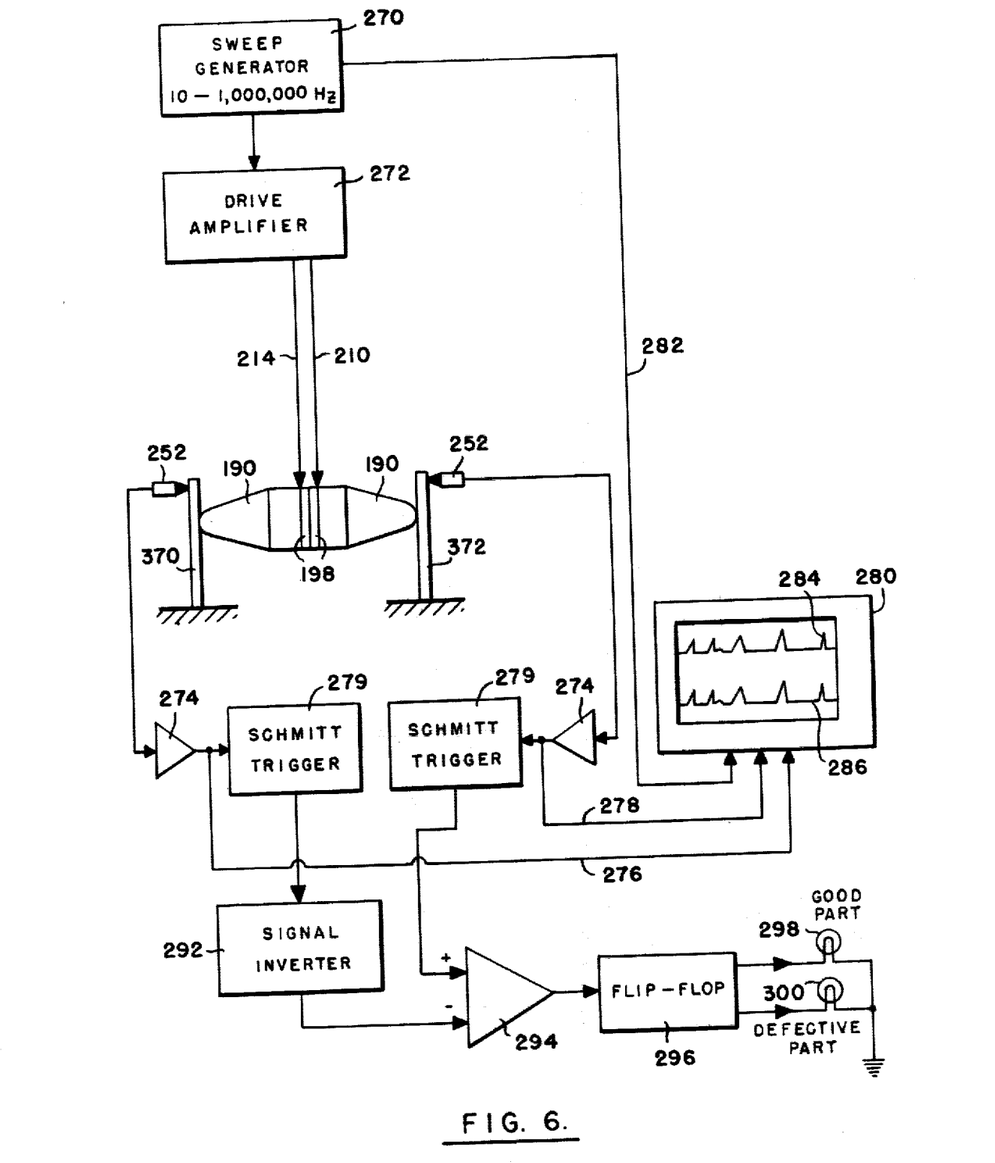
FIG. 6 is a block diagram of apparatus associated with the device of FIG. 1.

Referring now to FIG. 6, a sweep generator 270 having a sweeping frequency output range from 10 cycles per second to a million cycles per second supplies a sweep frequency selected by the operator, for example, from about 1,000 cycles to about 100,000 cycles per second to a drive amplifier 272, for example, a 50 watt linear amplifier of good high-fidelity quality. Amplifier output lines 214 and 210 are connected to amplifier 272 for the driving of crystals 198,198 and horns 190,190 in exact phase with respect to each other in opposite directions. The axial wave form of the motion are identical in both cases.

Each accelerometer 252 driven by the associated drive horn 190 feeds an associated operational amplifier 274 to achieve a gain of about 1,000. A typical part vibration amplitude for a resonance peak might produce an accelerometer output of 2 millivolts which would be boosted by the operational amplifier up to, for example, 2 volts for such a peak. Advantageously, the operational amplifiers are transistorized. The voltages supplied by the operational amplifiers 274,274 are delivered by lines 276 and 278, respectively, to separate channels of a display oscilloscope 280 which is also supplied with a ramp function horizontal input from sweep generator 270 as indicated by the line 282. The voltage increases on the ramp function as the sweep generator output frequency increases causing the traces of the oscilloscope channels to move from left to right so that the position of the traces are direct functions of frequency. On one channel of the oscilloscope, the input from line 276 produces a wave form trace (spectra) 284 generated by a test part and on another channel the input from line 278 produces a wave form trace (spectra) 286 from a standard part providing for a comparison of a test part with a standard part.

When it is desired to have a signal indicating whether the part being tested compares satisfactorily with a standard part, the voltages of the operational amplifiers 274,274 are supplied to Schmitt triggers 279,279 respectively. When the voltage coming out of each operational amplifier exceeds a predetermined value, for example, 1.5 volts, the associated Schmitt trigger will produce a standard wave form representing a particular resonance. The signal from one Schmitt trigger 279 is supplied to a signal inverter 292 and is then supplied to a differential amplifier 294. The signal from the other Schmitt trigger is supplied directly to differential amplifier 294. The output of differential amplifier 294 is the difference between the two input signals. The output of amplifier 294 is supplied to a flip-flop 296 controlling the supply of power to a signal lamp 293 indicating a good part and a signal lamp 300 indicating a defective part. If the two signals supplied to the differential amplifier 294 are coincident occurring in the same time frame and within the correct width set in the Schmitt triggers, the flip-flop 296 will remain in its normal state with lamp 298 being lighted indicating a good part and a lamp 300 being out. If on the other hand, the input signals to the differential amplifier 294 are substantially different causing a substantial output from the amplifier to flip-flop 296, then the state of flip-flop 296 will change shutting off power to light 298 and supplying power to light 300 indicating a defective part.

Figure 7:
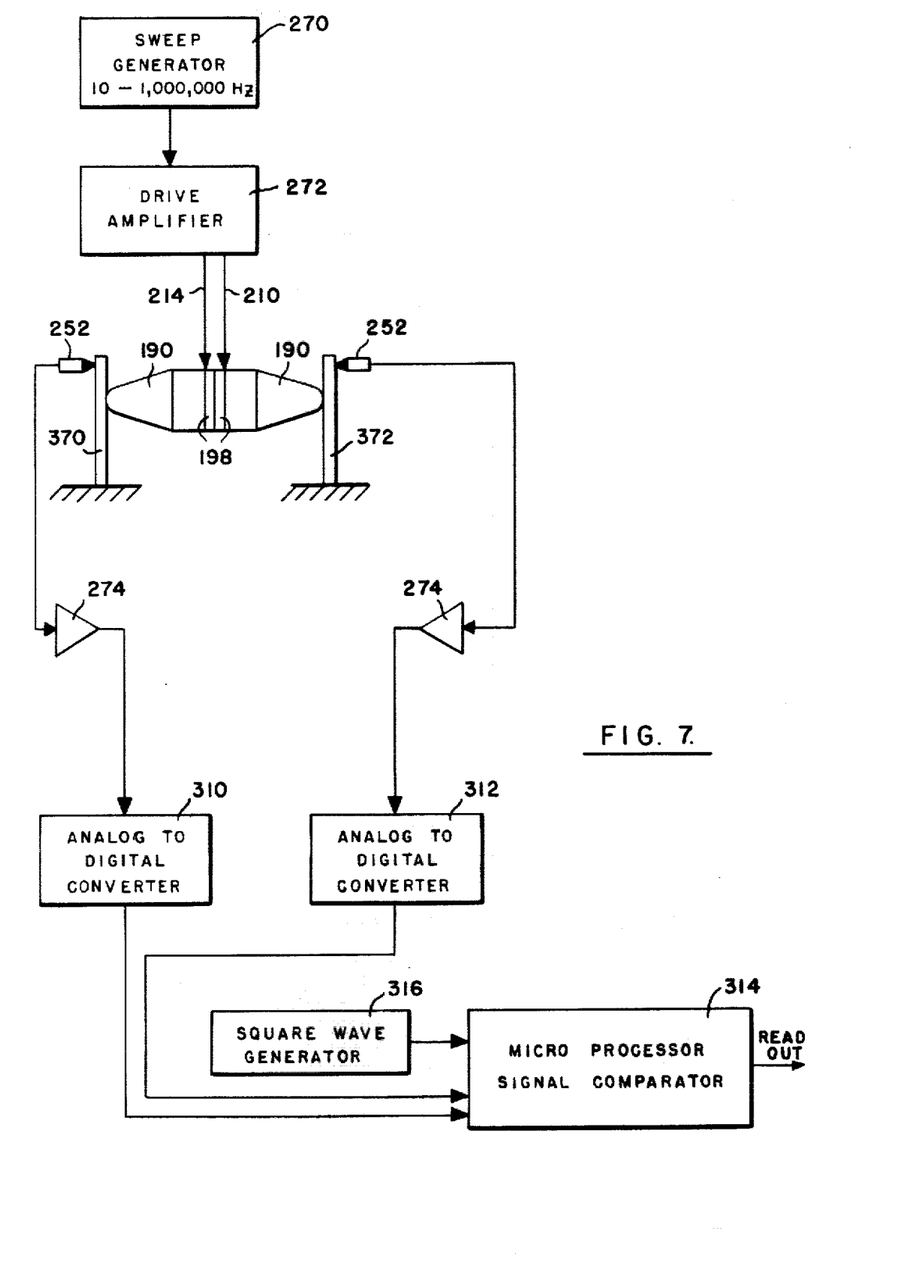
FIG. 7 is a block diagram of apparatus using a microprocessor to analyze the output signals of the accelerometer of the device of FIG. 1.

As shown in FIG. 7, an analysis of the output signals from the accelerometers 252,252 can be carried out with a signal comparator. Here, the signals from one operational amplifier 274 are supplied to an analog to digital converter 310 and the signals from the other operational amplifier 274 are supplied to an analog to digital converter 312. The signals from converters 310 and 312 are supplied to a microprocessor signal comparator 314. A square wave generator 316 oscillating at 2,000 cycles per second feeds into signal comparator 314 and is used to break the input signals from each of the converters 310 and 312 each into 2,000 separate data channels. The amplitude of each data channel of one signal is compared to the amplitude of the same data channel of the other signal and the differences are compared by the signal comparator. The use of signal comparators to compare signal amplitudes is well known to the art and, hence will not be further detailed. A wide variety of readouts are well known to be provided. The signal comparator 314 is set up in a well known manner to provide an indication as to whether the differences between the amplitudes of the signals received by the signal comparator are within acceptable limits, for example, having a difference not exceeding 20%.

Operation

By way of illustration of the operation of the testing device 2, it can be used to test a stator 370 of a jet engine. In order to carry out the test, stator 370 is compared with a stator 372 which is known to be without imperfections as a standard. At the commencement of operations the carriages 22 are further removed from plate 164 than is shown in FIG. 1. Similarly, chuck members 44 are positioned closer to their respective blocks 34 with jaw members 46 and 48 spaced apart ready for the reception of a part to be held. Each handle 90 is turned 180° from its position shown in FIG. 1.

Stator 370 is positioned between jaw members 46 and 48 as shown in FIG. 1 and the adjacent chuck member 44 advanced to the right is viewed in FIG. 1 by the rotation of handle 62, the hub 63 of which is against block 34 at this juncture. The rotation of handle 62 and consequently of nut 54 causes nut 54 to advance to the right as seen in FIG. 1 since the proximity of flanges 80 and 82 to chuck member 44 prevents nut 54 from rotating. The advancement of nut 54 causes flange 80 to bear against cam 84 thus causing the advancement to the right of chuck member 44. This operation is carried out until jaw member 46 lightly confines stator 370 between jaw members 46 and 48 and resting against guide arm 238. Handle 90 is then rotated 180° to place cam 84 in the position shown in FIG. 5. As cam 84 is thus rotated, the high part of the cam bears against flange 80 causing chuck member 44 to be moved to the right as shown in FIG. 4 and nut 54 and shaft 58 to move to the left. The movement of shaft 58 is resisted by compression coil spring 66 and hence the force exerted by jaw member 46 against stator 370 is substantially equal to the force exerted by the compression of spring 66 incident to its being compressed by the movement of cam 84 and rod 58. In this manner, it is possible to hold stator 370 with a predetermined force and by the same procedure to hold the standard stator 372 with the same predetermined force. This is important for the achievement of accuracy in the test.

The height of horns 190,190 is now adjusted by rotating handle 158 to turn threaded rod 154 in bracket 162. Switch 123 is closed causing DC permanent magnet motor 114 which has self-contained reduction gears to drive threaded shaft 104 causing the advancement of nut 106 to the right as viewed in FIG. 4. Nut 106 is prevented from rotating by the proximity of its top 108 to bracket 94. Nut 106, bearing against compression coil spring 110 which in turn bears against arm 100 of bracket 94, causes carriage 22 to be advanced. The advancement of carriage 22 carries stator 370 into contact with the nose 192 of the adjacent horn 190 which in turn causes nut 106 to compress spring 110 until nut 106 moves sufficiently far away from switch 112 to permit it to open and stop the rotation of motor 114. This results in stator 370 exerting a predetermined force against nose 192. Since stator 372 is handled in the same fashion, the force exerted by stators 370 and 372 against their respective horns 190,190 will be the same. Here again, this provides for accuracy in the test results.

The accelerometers 252,252 are now placed in contact with stators 370 and 372, respectively, being held in position by leaf springs 250. The leaf springs hold the accelerometers against the stators with the same force preferably within a limit of plus or minus 10 grams. Preferably, also the accelerometers are positioned at the same point on the stators within a limit of accuracy of plus or minus 0.1 cm. Comparable accuracy is important with regard to the relationship between the stators and the horns where the force will be the same, preferably within plus or minus 20 grams and the horns will bear on the same spot of the stators preferably within plus or minus 0.1 cm. While these figures will vary with different parts, they are indicative of the fact that accuracy of positioning and forces is necessary which is made possible by the invention.

The electronic apparatus shown in FIG. 6 is now activated with the sweep generator 270 and drive amplifier 272 causing crystals 198,198 to vibrate drive horns 190,190 and in turn vibrate stators 370 and 372.

The vibration of stators 370 and 372 is converted to electrical signals by accelerometers 252,252 the outputs of which are amplified by amplifiers 274,274 whose outputs are supplied to oscilloscope 280 where a display of the vibrations is shown at 284 and 286. A skilled operator by observing a comparison between the vibrations of the test part 370 which are displayed at 284, and the vibrations of the standard part 372 which are displayed at 286, can determine whether or not the part 370 is satisfactory by comparing the closeness of the coincidence and amplitude of the peaks of the curves displayed, closeness in coincidence and amplitudes indicating that the part 370 being tested is satisfactory.

If the operator does not wish to use the oscilloscope 280, he can observe the lamps 298 and 300, lamp 298 being lighted indicating a good part and lamp 300 being lighted indicating a bad part. The lights are appropriately activated by virtue of the outputs going from amplifiers 274,274 to Schmitt triggers 279,279 with their outputs being supplied to a differential amplifier 294, one of the signals being inverted. Absent any signal from differential amplifier 294, flip-flop 296 is in a state causing power to be delivered to lamp 298 and no power to be delivered to lamp 300. In the event that there is a difference between resonance peaks of stators 370 and 374, differential amplifier will have an output signal which will cause the flip-flop 296 to change its state causing power to be shut-off from lamp 298 and delivered to lamp 300 indicating a defective part.

Alternatively, a signal comparator 314 is used in the manner described above.

After the test is completed, stator 370 is removed by reversing the left-hand motor 114 as seen in FIG. 1 by closing switch 130 to remove the stator 370 from adjacent horn 190. This causes nut 106 to bear against arm 98 and move the bracket 94 and carriage 22 to the left as seen in FIG. 4 and closes switch 113 by depressing switch button 112 to a point flush with arm 98. Motor 114 stops when bracket 94 opens switch 135. Handle 190 is then turned 180° which frees stator 370 sufficiently for withdrawal. The standard stator 372 is left in position for the testing of the next stator to be tested.

Alternative Embodiment

Figure 8:
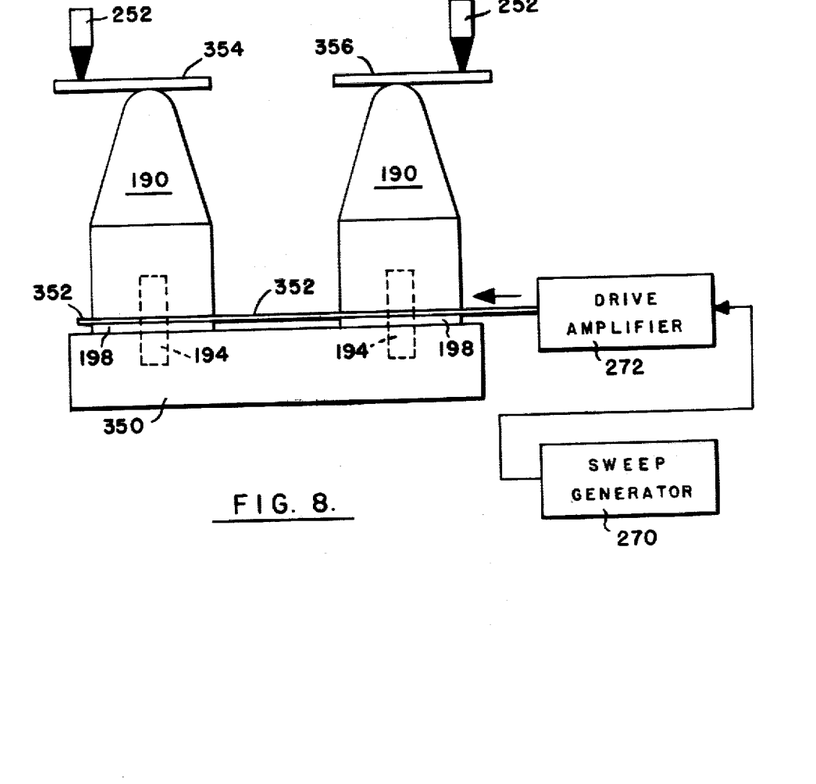
FIG. 8 is a diagrammatic view of an alternative embodiment of the invention in which the drive horns are in a parallel relationship.

The drive horns to vibrate the standard and the part to be tested may be in a wide variety of spacial relationships other than coaxial as in the device of FIG. 1. By way of illustration, as shown in FIG. 8, drive horns 190,190 may be in a parallel relationship. As shown in FIG. 8, drive horns 190,190 are mounted above crystals 198,198, respectively, which in turn are mounted on a metal block 350 of, for example, steel or aluminum which acts as a reaction mass. Interposed between each crystals 198 and drive horns 190 is a metal conducting sheet 352 of, for example, aluminum. Each drive horn 190 and crystal 198 together with sheet 352 is secured to block 350 by a threaded insulator 194. Sweep generator 270 drives amplifier 272 whose output is supplied to sheet 352 and thence to crystals 198,198. One horn 190 engages a test part 354. The other horn 190 engages a standard part 356 of known quality. An accelerometer 252 is connected to each part 354 and 356 with the output of the accelerometers 252 being handled in the same fashion as the output of the accelerometers 252,252 shown in FIG. 6. The device of FIG. 8 can be used also to test a relatively large part of uniform structure by placing the horns on different areas of the part in which event a disconformity of the output signals will indicate a flaw in the part.

I claim:

1. A device for detecting flaws in a test part comprising:
   a sweep generator,
   a drive amplifier supplied by the sweep generator,
   a pair of electrical to mechanical transducers connected to the amplifier,
   a first carriage associated with one transducer for a test part,
   a second carriage associated with the other transducer for a standard part,
   means for moving each carriage towards and away from its associated transducer,
   means on each carriage for holding a part,
   an accelerometer associated with each carriage for contacting a part on the carriage, and
   means responsive to the signals from the accelerometers for the comparison of the signals.

2. A device in accordance with claim 1 in which the means for holding a part on the carriages holds the parts with substantially the same force.

3. A device in accordance with claim 1 in which the means for moving the carriages includes means for holding the parts against their associated transducers with substantially the same force.

4. A device in accordance with claim 1 having means to hold the accelerometer against their associated parts with substantially the same force.

5. A device in accordance with claim 1 in which the means for holding a part on the carriages holds the parts with substantially the same force, and in which the means for moving the carriages includes means for holding the parts against their associated transducers with substantially the same force, and having means to hold the accelerometer against their associated parts with substantially the same force.

6. A device in accordance with claim 1 having means to adjust the elevation of the transducers.

7. A device in accordance with claim 1 in which the responsive means includes an oscilloscope.

8. A device in accordance with claim 1 in which the responsive means includes a signal comparator.

9. A device in accordance with claim 1 in which the means for moving each carriage includes a motor, a first member adapted to be advanced towards the associated transducer by the motor, a resilient member interposed between the first member and the carriage, a switch in contact with the trailing end of the first member for stopping the motor when the spring is compressed a predetermined amount incident to contact between the part mounted on the carriage and the associated transducer to provide for the parts to be held against their associated transducers with substantially the same force.

10. A device in accordance with claim 1 in which the means for holding a part comprises a chuck and a resilient member for holding the chuck closed for holding the part on each carriage with substantially the same predetermined force.

11. A device in accordance with claim 1 in which the means for holding a part comprises a chuck having a movable and a fixed portion, a rotatable cam mounted on the movable portion, a nut having a recess for the reception of the cam and held against rotation by the said movable portion, a shaft threaded to the nut for movement of the movable portion of the chuck through the cam, resilient means for resisting the movement of the shaft away from the fixed portion of the chuck whereby the rotation of the threaded member is adapted to bring the movable portion into contact with a part between the movable portion and the fixed portion and the cam is adapted to urge the movable portion against the part and the shaft through the nut against the resilient means for holding the parts on the carriages with substantially the same force.

12. A device in accordance with claim 1 in which the means for moving each carriage includes a motor, a first member adapted to be advanced towards the associated transducer by the motor, a resilient member interposed between the first member and the carriage, a switch in contact with the trailing end of the first member for stopping the motor when the spring is compressed a predetermined amount incident to contact between the part mounted on the carriage and the associated transducer to provide for the parts to be held against their associated transducer with substantially the same force, and in which the means for holding a part comprises a chuck having a movable and a fixed portion, a rotatable cam mounted on the movable portion, a nut having a recess for the reception of the cam and held against rotation by the said movable portion, a shaft threaded to the nut for movement of the movable portion of the chuck through the cam, resilient means for resisting the movement of the shaft away from the fixed portion of the chuck whereby the rotation of the threaded member is adapted to bring the movable portion into contact with a part between the movable portion and the fixed portion and the cam is adapted to urge the movable portion against the part and the shaft through the nut against the resilient means for holding the parts on the carriages with substantially the same force.

13. A device for detecting flaws in a test part comprising:
a pair of electrical to mechanical transducers,
means to drive the transducers in phase and at the same frequency,
a first carriage associated with one transducer for a test part,
a second carriage associated with the other transducer for a standard part,
means for moving each carriage towards and away from its associated transducer,
means on each carriage for holding a part,
an accelerometer associated with each carriage for contacting a part on the carriage, and
means responsive to the signals from the accelerometers for the comparison of the signals.

14. A device for detecting flaws in a test part comprising:
electrical to mechanical transducer means for inducing the same variable frequency mechanical vibrations in the test part and in a standard part,
means for placing and maintaining each of said parts in contact with said transducer means with substantially the same force,
means for comparing the structural integrity of said parts when they are being vibrated, including an accelerometer for contacting the test part and an accelerometer for contacting the standard part for respectively producing electrical signals analogous to the vibrations of the test part and the standard part, and
means for placing and maintaining each accelerometer in contact with its respective part with substantially the same force.

* * * * *